United States Patent
Leung et al.

(10) Patent No.: US 9,657,044 B2
(45) Date of Patent: May 23, 2017

(54) METHOD FOR ANTAGONIZING STAT3 DIMERIZATION AND COMPOUNDS FOR USE THEREIN

(71) Applicants: University of Macau, Taipa, Macau (CN); Hong Kong Baptist University, Kowloon (HK); Kaohsiung Medical University, Kaohsiung (TW)

(72) Inventors: Chung-Hang Leung, Macau (CN); Dik-Lung Ma, Kowloon (HK); Hui-Min Wang, Kaohsiung (TW)

(73) Assignees: University of Macau, Macau (CN); Hong Kong Baptist University, Kowloon (HK); Kaohsiung Medical University, Kaosiung (TW)

(*) Notice: Subject to any disclaimer, the term of this patent is extended or adjusted under 35 U.S.C. 154(b) by 0 days.

(21) Appl. No.: 15/168,556

(22) Filed: May 31, 2016

(65) Prior Publication Data
US 2016/0347779 A1 Dec. 1, 2016

Related U.S. Application Data

(60) Provisional application No. 62/168,371, filed on May 29, 2015.

(51) Int. Cl.
C07F 15/00 (2006.01)
(52) U.S. Cl.
CPC .................. *C07F 15/0073* (2013.01)
(58) Field of Classification Search
None
See application file for complete search history.

(56) References Cited

PUBLICATIONS

Database CAPLUS Chemical Abstracts Service, Columbus, Ohio, US; Database Accession No. 2014:886685, Abstract of Ma et al., Angewandte Chemie, International Edition (2014), 53(35), 9178-9182.*
Database CAPLUS Chemical Abstracts Service, Columbus, Ohio, US; Database Accession No. 1987:84824, Abstract of Ohsawa et al., Journal of Physical Chemistry (1987), 91(5), 1047-54.*

(Continued)

*Primary Examiner* — Karl J Puttlitz
(74) *Attorney, Agent, or Firm* — Ladas & Parry LLP

(57) ABSTRACT

A compound of the formula:

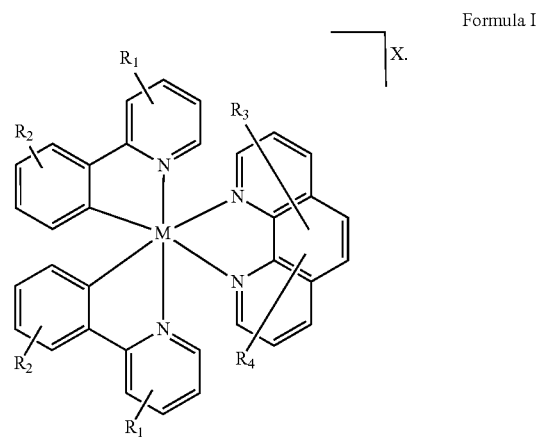

Formula I

Also, a method for antagonizing STAT3 dimerization in a patient in need thereof which by administering to such patient a therapeutically acceptable dose of the compound of Formula I. Further, a method for treating a cancer patient in need thereof by administering a therapeutically effective dose of the compound of Formula I.

22 Claims, 1 Drawing Sheet

Dose response effect of the compound of Formula II on different cancer cell lines.

(56) References Cited

PUBLICATIONS

Database CAPLUS Chemical Abstracts Service, Columbus, Ohio, US; Database Accession No. 1988:454943, Abstract of Sandrini et al., Inorganic Chemistry (1988), 27(15), 2640-.*
Database CAPLUS Chemical Abstracts Service, Columbus, Ohio, US; Database Accession No. 2003:79488, Abstract of Lo et al., Chemistry—A European Journal (2003), 9(2), 475-483.*
Cao et al., J. Med. Chem. 2013, 56, 3636-3644.*
Leung et al., Chemical Communications (Cambridge, United Kingdom) (2015), 51(19), 3973-3976.*
Ma et al., Angew. Chem. Int. Ed. 2014, 53, 9178-9182.*
Dragonetti et al., Inorganic Chemistry, vol. 46, No. 21, 2007.*
Yu, H., et al., "STATs in cancer inflammation and immunity: a leading role for STAT3", Nat. Rev. Cancer Nov. 2009, 9(11), 798-809.
Garcia, R, et al., "Constitutive activation of Stat3 by the Src and JAK tyrosine kinases participates in growth regulation of human breast carcinoma cells", Oncogene 2001, 20, 2499-2513.
Bowman, T., et al., "STATs in oncogenesis", Oncogene, 2000, 19, 2474-2488.
Niu, G., et al., "Constitutive Stat3 activity up-regulates VEGF expression and tumor angiogenesis", Oncogene 2002, 21, 2000-2008.
Pedranzini, L, et al., "Stat3 is required for the development of skin cancer", J Clin. Invest. Sep. 2004, 114(5), 619-622.
Song, L., et al., "Activation of Stat3 by receptor tyrosine kinases and cytokines regulates survival in human non-small cell carcinoma cells", Oncogene 2003, 22, 4150-4165.
Zhou, C., et al.,, "PTTG Acts As a STAT3 Target Gene for Colorectal Cancer Cell Growth and Motility", Oncogene. Feb. 13, 2014, 33(7), 851-861.
Wang, T., et al., "Prosapogenin A induces apoptosis in human cancer cells in vitro via inhibition of the STAT3 signaling pathway and glycolysis", Oncology Letters, 2013, 6, 1329-1328.
Wang, S., et al., "Establishment and Characterization of MTDH Knockdown by Artificial MicroRNA Interference—Functions as a Potential Tumor Suppressor in Breast Cancer", Asian Pac. J. Cancer Prev. 2012, 13, 2813-2818.
Siddiquee, K, et al., "An Oxazole-Based Small-Molecule Stat3 Inhibitor Modulates Stat3 Stability and Processing and Induces Antitumor Cell Effects", ACS Chem. Biol. Jun. 7, 2007, 2(12), 787-798.
Li, H., et al., "Fragment-Based Drug Design and Drug Repositioning Using Multiple Ligand Simultaneous Docking (MLSD): Identifying Celecoxib and Template Compounds as Novel Inhibitors of Signal Transducer and Activator of Transcription 3 (STAT3)", J. Med. Chem. 2011, 54, 5592-5596.
Chen, H., et al., "Fragment-based drug design and identification of HJC0123, a novel orally bioavailable STAT3 inhibitor for cancer therapy", Eur. J. Med. Chem. Apr. 2013, 62, 498-507.
Zhang, X, et al., "Orally bioavailable small-molecule inhibitor of transcription factor Stat3 regresses human breast and lung cancer xenografts", Proc. Nat. Acad. Sci., Jun. 12, 2012, 109(24), 9623-9628.
Siddiquee, K, et al., "Selective chemical probe inhibitor of Stat3, identified through structure-based virtual screening, induces antitumor activity", Proc. Nat. Acad. Sci., May 1, 2007, 104(18), 7391-7396.
Leung, C., et al., "A Metal-Based Inhibitor of Tumor Necrosis Factor-α", Angew. Chem. Int. Ed., 2012, 51, 9010-9014.
Zhong, H, et al., "Antagonism of mTOR Activity by a Kinetically Inert Rhodium(III) Complex", ChemPlusChem, 2014, 79, 508-511.
Lowry, M., et al., "Accelerated Luminophore Discovery through Combinatorial Synthesis", J. Am. Chem. Soc. 2004, 126, 14129-14135.
Ma, D, et al., "Antagonizing STAT3 Dimerization with a Rhodium(III) Complex", Angew. Chem. Int. Ed., 2014, 53, 9178-9182.
Lin, Y, et al., "Organometallic ruthenium anticancer complexes inhibit human glutathione-S-transferase π", J. Inorg. Biocherm., 2013, 128, 77-84.

* cited by examiner

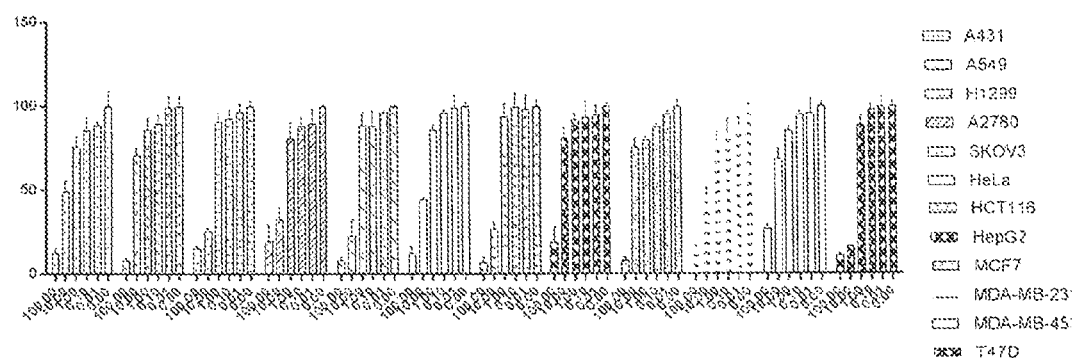
Dose response effect of the compound of Formula II on different cancer cell lines.

METHOD FOR ANTAGONIZING STAT3 DIMERIZATION AND COMPOUNDS FOR USE THEREIN

RELATED APPLICATIONS

The present application claims priority from provisional application 62/168,371 filed on May 29, 2015, the contents of which are incorporated herein by reference.

FIELD OF THE INVENTION

The present invention relates to a method for antagonizing STAT3 dimerization using rhodium(III) or iridium(III) complexes and to novel complexes for such use.

BACKGROUND OF THE INVENTION

As described by H Yu et al *Nat. Rev. Cancer* 2000, 9, 798-809, the signal transducer and activator of transcription (STAT) family proteins mediate a range of cellular responses to cytokines and growth factors. R Garcia et al *Oncogene* 2001, 20, 2499-2513 note the activation of STAT proteins is initiated by upstream growth factor receptors and cytoplasmic kinases such as Janus kinases (JAKs) and Src family kinases, thus culminating in the formation of activated STAT dimers by reciprocal phosphotyrosine-Src Homology 2 (SH2) domain interactions. T Bowman et al *Oncogene*, 2000, 19, 2474-2488 have reported the aberrant expression and constitutive activation of one of the STATs, STAT3, has been associated with tumorgenesis through upregulation of cell survival proteins and cell-cycle regulators, and G. Nu et al *Oncogene* 2002, 21, 2000-2008 reported enhanced angiogenesis of cells. In particular, L. Pedranzini et al *J. Clin. Invest.* 2004, 112, 629-622 and others have reported that STAT3 plays an important role in the development of skin cancer. Lanxi Song et al *Oncogene* 2003, 22, 4150-4165 discuss activation of STAT3 by receptor tyrosine kinases and cytokines and conclude that direct inhibition of STAT3 leads to apoptotic cell death in nonsmall cell lung carcinomas and that experiments with A549 and H1299 cells and suggest that STAT3 controls apomotic pathways in certain human lung cancer cells. C. Zhou at al *Oncogene.* 2014, 33, 851-861 note that STAT3 likely regulates a group of genes that control apoptotic pathways in a number of human cancer models, including breast (MCF7, MDA-MB-231, MDA-MB-453 and T47D cells), myeloma, colorectal (HCT116), prostate, pancreatic, ovarian (A2780 and SKOV3) and head and neck squamous cell carcinomas and various hematological malignancies. Blocking the STAT3 signaling pathway has been reported as inducing growth inhibition and apoptosis in human cervical cancer HeLa cells, human hepatocellular HepG2 cells, and skin squamous cell carcinoma A431 cells. (*Oncol, Lett.* 2013, 6, 1323-1328; *Asian Pac. J. Cancer Prev.* 2015, 16, 2813-2818).

The inhibition of STAT3 dimerization through occupation of the SH2 domain of STAT3 has been demonstrated by a number of small molecules. K. A. Siddiquee, et al *ACS Chem. Biol.* 2007, 2, 787-798; H. Li, et al *J. Med. Chem.* 2011, 54, 5592-5596 H. J. Chen, et al *Eur. J. Med. Chem.* 2013, 62, 498-507; and X. L. Zhang, et al *Proc. Natl. Acad. Sci. USA* 2012, 109, 9623-9628.

K. Siddiquee, et al *Proc. Natl. Acad. Sci. USA* 2007, 104, 7391-7396 have reported that S3I-201 (NSC 74859) induced the regression of human breast cancer xenografts in a nude mice model.

Sadler and coworkers developed organometallic ruthenium(II) anticancer complexes which exhibit in vitro and in vivo anticancer activities by inhibition of human glutathione-S-transferase π. (Y. Lin, et al *J. Inorg. Biochem.* 2009, 9, 798-809.) Recently, our group reported the first examples of rhodium(III) and iridium(III) complexes as inhibitors of the NEDD8-activating enzyme (NAE), tumor necrosis factor α (TNF-α), and the mammalian target or rapamycin (mTOR). (*Angew. Chem.* 2012, 124, 9144-9148; *Angew. Chem. Int. Ed.* 2012, 51, 9010-9014; *Chem Plus Chem* 2014, 79, 508-511)

SUMMARY OF THE INVENTION

From a first aspect, the present invention provides novel compounds of the formula:

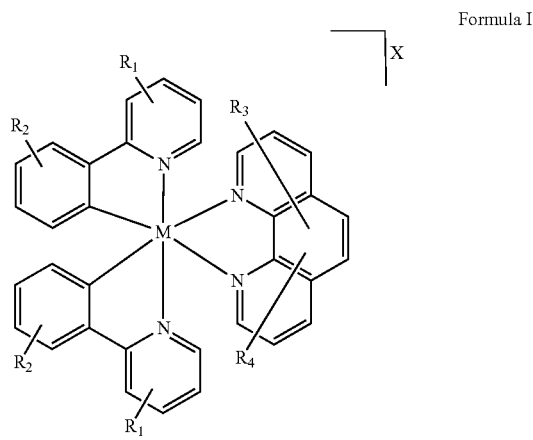

Formula I wherein

M represents iridium or rhodium;

X represents an anion selected from the group consisting of fluorine, chlorine, bromine, nitrate, tetrafluoroborate, hexafluorophosphate ($PF_6$), trifluoromethane solfonate, trifluoromethane sulfonimide, acetate, trifluoroacetate, tetraphenyl borate, toluene sulfonate, dodecylbenzene sulfonate and mixtures thereof;

$R^1$ and $R^2$ independently represent H, F, Cl, —O-alkyl, —CH=O, —C(=O)—O-alkyl, —C(=O)—$CF_3$, —$CF_3$, branched or unbranched alkyl, alkyl ether, unsubstituted or substituted phenyl, fluorene, spirofluorene, sulfonate, or 4-sulfonato-phenyl.

or $R^1$ and $R^2$ together represent —CH=CH—, —CH=CH—CH=CH—;

$R^3$ and $R^4$ may be substituents to any of the rings of the phenanthroline ligand and independently represent H, Cl, —O-alkyl, —$CH_3$, —$C_2H_5$, —CH=O, —C(=O)—O-alkyl, —$CF_3$, branched or unbranched alkyl ether, unsubstituted or substituted phenyl.

or $R^3$ and $R^4$ together represent —CH=CH—CH=CH—, —CH=C($CH_3$)—C($CH_3$)=CH—.

When used herein the term "alkyl" means an alkyl group that preferably has from 1-8 carbon atoms, and by way of example has from 1-6 carbon atoms, or from 1-3 carbon atoms.

Substituted phenyl groups include phenyl groups substituted by F, Cl, —O-alkyl, —$CH_3$, —$C_2H_5$, —CH=O, —C(=O)—O-alkyl, —$CF_3$, branched or unbranched alkyl, alkyl ether groups.

From a second aspect, the present invention provides a method for antagonizing STAT3 dimerization in a patient in need thereof which comprises administering to such patient a therapeutically effective dose of a compound of Formula I.

From a third aspect, the present invention provides a method for treating a cancer patient in need thereof by administering a therapeutically effective dose of a compound of Formula I and in particular treating patients suffering from nonsmall cell lung carcinoma, breast cancer, colorectal cancer, ovarian cancer, cervical cancer, hepatocellular cancer or skin cancer.

BRIEF DESCRIPTION OF THE DRAWING

The FIGURE depicts the dose response effect of the compound of Formula II described below on the viability of different cancer cells.

DETAILED DESCRIPTION OF THE INVENTION

Particularly preferred compounds of the present invention and for use in the methods noted above such as antagonizing STAT3 dimerization and treating various cancers are those of Formula I wherein M is rhodium, X is $PF_6$, $R^1$ is hydrogen, fluorine, chlorine or substituted phenyl, $R^2$ is CHO, $R^3$ and $R^4$ independently represents H, F, Cl, —O-alkyl, —$CH_3$, —$C_2H_5$. Preferably $R^3$ and $R^4$ are bound to the central ring of the phenanthroline ligand.

A particularly preferred compound is of the formula:

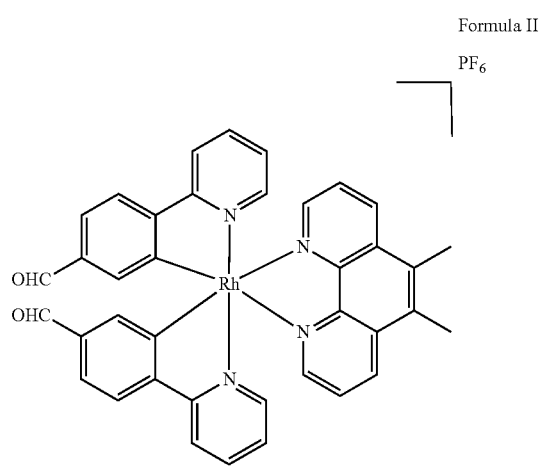

Formula II

Compounds of the present invention may be prepared using a modification of the method described by M. S. Lowry et al *J. Am. Chem. Soc.* 2004, 126, 14129-14135, Rhodium(III) chloride is reacted with a compound of Formula III

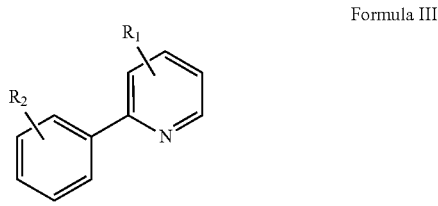

Formula III for example by heating at a temperature from 120-170° C. in a solvent under an inert atmosphere. The product is isolated and then reacted with a compound of Formula IV

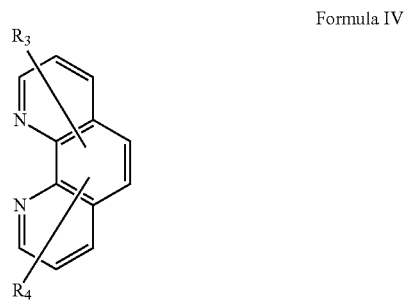

Formula IV for example by heating in an alcohol/chlorinated hydrocarbon solvent, such as methanol/dichloromethane with reflux. The product may be recovered from the solution resulting from this reaction by precipitation using a salt having a non-coordinating anion such as a hexaflurophosphate or tetralluoroborate.

In a particularly useful synthesis, $RhCl_3 \cdot nH_2O$ is heated to 150° C. with 2.2 equivalent of a compound of Formula III in 3:1 methoxyethanol and deionized water under nitrogen atmosphere for 12 h. The product was filtered off and washed with ether (3×50 mL) and then with deionized water (3×50 mL). A suspension of $[M_2(C^{\wedge}N)_4Cl_2]$ (0.2 mmol) and a compound of Formula IV (0.44 mmol) in a mixture of DCM:methanol (1:1, v/v, 20 mL) was refluxed overnight under a nitrogen atmosphere. The resulting solution was then allowed to cool to room temperature, and filtered to remove unreacted cyclometallated dimer. To the filtrate, an aqueous solution of ammonium hexafluorophosphate (excess) was added and the filtrate was reduced in volume by rotary evaporation until precipitation of the crude product occurred. The precipitate was then filtered and washed with several portions of water (2×50 mL) followed by diethyl ether (2×50 mL). The product was recrystallized by acetonitrile:diethyl ether vapor diffusion to yield the titled compound. All complexes are characterized by $^1$H-NMR, $^{13}$C-NMR and high resolution mass spectrometry (HRMS) and elemental analysis. Stability analysis of complexes. All the 35 complexes were stored in DMSO-$d_6$:$D_2O$ (9:1, v/v; 5 mM) at 298K for seven days, and were determined by $^1$H NMR spectroscopy. $^1$H NMR experiments were performed with a Bruker Avance 400 spectrometer (Bruker Avance-III, UltraShield Magnet).

The novel cyclometalated rhodium(III) or iridium(III) complex of the invention such as that of Formula II can act as a direct inhibitor of STAT3. The compound of Formula II targets the SH2 domain of STAT3, as revealed by a fluorescence polarization assay, and was able to inhibit STAT3 DNA binding activity in vitro and attenuate STAT3 phosphorylation, dimerization, and signaling activity in cells. Importantly, the compound of Formula II was able to significantly reduce tumor size and weight in an in vivo mouse xenograft model. Furthermore, tumor tissues treated with the compound of Formula II showed repressed STAT3 phosphorylation, vascular endothelial growth factor (VEGF) expression, and angiogenesis.

Compounds of the invention may be useful in prevention of oncogenesis and the treatment of cancers, such as colon cancer and brain cancer where STAT3 phosphorylation and dimerization is of particular relevance.

Without wishing to be bound by any theory, the inventors believe that the anti-tumor effects of the compound of Formula II in the mouse model is mediated, at least in part, by the inhibition of STAT3-directed gene expression by the compound of Formula II in vivo, which could in turn be attributed to its ability to target the SH2 domain of STAT3 and inhibit STAT3 dimerization. The inventors anticipate that the rhodium(III) complexes of the present invention serve as useful inhibitors of STAT3 dimerization as potential anti-neoplastic agents.

Compounds of the present invention may be administrated to patients in need thereof in a variety of forms. These include, for example, solid, semi-solid and liquid dosage forms, such as tablets, pills, powders, liquid solutions or suspensions, liposome preparations, injectable and infusible solutions. The preferred form depends on the intended mode of administration and therapeutic application. The compositions also preferably include conventional pharmaceutically acceptable carriers and adjuvants which are known to those of skill in the art. See, e.g., Remington; The Science and Practice of Pharmacy, Ed. Randy Hendrickson, Lippincott, Williams & Wilkins, 21st Edition (2005). For example oral formulations may include such typical excipients as, for example, pharmaceutical grades of mannitol, lactose, starch, magnesium stearate, sodium saccharine, cellulose, magnesium carbonate and the like.

Generally, administration will be by oral or parenteral (including subcutaneous, intramuscular, intravenous, and intradermal) routes, or by topical application or infusion into a body cavity, or as a bathing solution for tissues during surgery. Oral dosage forms may be sustained dosage formulations in which the particles of the active compound are coated so as to delay release into the blood stream for example by coating with a pharmaceutically acceptable polymer that is dissolved in gastric juices such as polyvinyl pyrrolidone and then sizing the particles and incorporating specific ratios of particles of particular sizes into a tablet, capsule or lozenge so that particles having different degrees of thickness of coating are released at different times, or using a controlled-release device which employs osmosis.

Compositions for parenteral administration are preferably water-based and may contain salt and/or HCl to adjust the pH. A typical parenteral composition may contain the compound of Formula II (75 mg/kg) and PBS (pH7.4, 137 mM NaCl, 2.7 mM KCl, 4.3 mM $Na_2HPO_4$, 1.47 mM $KH_2PO_4$). Water miscible co-solvent systems comprising solutions of water and water miscible solvents such as alcohol, glycerin, propylene glycol, polyethylene glycol 400 are known in the art and the compositions described herein may be formulated with such a co-solvent system for parenteral administration.

When the administration route is topical, the rhodium or iridium compound of Formula I may be administered in the form of a cream, ointment, salve or spray. Suitable excipients may include for example, animal and vegetable fats, oils, waxes, paraffins, starch, tragacanth, cellulose derivatives such as sodium carboxymethylcellulose, polyethylene glycols, silicones, bentonites, silicic acid, talc and zinc oxide, polyacrylates, polyoxyethylene-polyoxypropylene-block polymers, polyethylene glycol, wood wax alcohols and mixtures thereof.

The required dosage will depend upon the nature of the disease, the severity and course of the disease, previous therapy, the patient's health status and response to the rhodium or complex, and the judgment of the treating medical care giver.

In general for treatment of neoplastic diseases, a suitable effective dose of rhodium(III) or iridium(III) complex will be in the range of 0.01 to 1000 milligram (mg) per kilogram (kg) of body weight of recipient per day, preferably in the range or 1 to 100 mg per kg of body weight per day. The desired dosage is preferably presented in one, two, three, four or more subdoses administrated at appropriate intervals throughout the day. These sub-doses can be administrated as unit dosage forms, for example, containing 5 to 10,000 mg, preferably 10 to 1000 mg of active ingredient per unit dosage form.

Treatment with compounds of Formula I can be combined with other types of cancer treatment including radiation (including X-ray radiation, UV-radiation, gamma-radiation, or microwave radiation) and surgical removal of cancerous tissue. In some cases, combination chemotherapy may be useful, for example co-administering compounds of Formula I with known anti-cancer drugs such as verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate.

EXAMPLES

The invention is illustrated by the following examples.

Cytotoxicity Evaluation

In a preliminary cytotoxicity evaluation, the compound of Formula II exhibited potent cytotoxicity against A375.S2 ($IC_{50}$=6.6±3.0 μM) and A2058 ($IC_{50}$<1 mM) human melanoma cells, moderate cytotoxicity towards A375 human melanoma cells ($IC_{50}$=17.2±4.9 μM), but only low cytotoxicity towards HaCAT human keratinocytes ($IC_{50}$>100 μM) and normal human dermal fibroblasts ($IC_{50}$>100 μM). In contrast, a compound similar to that of Formula II but in which the group of Formula I has $R^3$ and $R^4$ as methyl showed a reduced ability to effectively discriminate between cancerous and normal cells.

The compound of Formula II was tested further as follows.

Methodology

The effect of the compound of Formula II on the growth of 12 different cancer cell lines including human epidermoid carcinoma cell line A431, human lung cancer cell lines A549 and H1299, human ovarian cancer cell lines A2780 and SKOV3, human cervical cancer cell line HeLa, human liver carcinoma cell line HepG2, human colon cancer cell line HCT116 and human breast cancer cell lines MCF7, MDA-MB-231, MDA-MB-453 and T47D was investigated using the MTT (3-(4,5-dimethylthiazol-2-yl)-2,5-diphenyltetrazolium bromide) cytotoxicity assay. The cells were treated with the compound of Formula II at different concentrations ranging from 0.1-100 μM. Drug-treated cells were incubated with MTT for 4 h at 37° C. in a humidified atmosphere of 5% $CO_2$ after 72 h drug treatment. The cells were maintained in a dark, humidified chamber overnight. After lysis, the formation of formazan were measured by using a microtitre plate reader at 550 nm. Each growth inhibition experiment were repeated for at least three times to obtain a result expressed as mean±standard deviation (SD). IC$_{50}$ values obtained are shown in the following table.

TABLE 1

IC$_{50}$ values of the compound of Formula II on different cancer cell lines.

| Cell Type | IC$_{50}$/µM |
|---|---|
| A431 | 6.698 ± 0.056 |
| A549 | 18.52 ± 0.042 |
| H1299 | 4.73 ± 0.040 |
| A2780 | 5.223 ± 0.071 |
| SKOV3 | 4.156 ± 0.047 |
| HeLa | 8.027 ± 0.023 |
| HCT116 | 5.262 ± 0.36 |
| HepG2 | 30.85 ± 0.424 |
| MCF7 | 20.58 ± 0.159 |
| MDA-MB-231 | 6.605 ± 0.062 |
| MDA-MB-453 | 25.4 ± 0.380 |
| T47D | 3.581 ± 0.032 |

The dose response effect of the compound of Formula II on the viability of different cancer cell is shown in the FIGURE.

Conclusion

The compound of Formula II shows a significant toxicity toward 12 different cancer cell lines with the most sensitivity on human ovarian cancer cell lines A2780 and SKOV3, human colon cancer cell line HCT116 and human breast cancer cell line T47D.

Activity in Mouse Xenograft Tumor Model

Given the promising anti-proliferative activity exhibited by the compound of Formula II in vitro, the inventors investigated the biological efficacy of this compound in a mouse xenograft tumor model, BALB/c nu/nu mice were injected subcutaneously with human malignant melanoma A375 cells, and were treated four times a week with a subcutaneous injection of either compound of Formula II (75 mg/kg) or a control until sacrifice at day 35. The tumors at sacrifice were visibly smaller in the treatment groups compared to the vehicle control group. Furthermore, there was a significant difference in the estimated tumor volume in the two groups from day 16 onwards. The mean tumor weight after sacrifice in the treatment group was reduced by about 60% compared to that of the control group. The inventors observed that the treated mice exhibited no signs of gross toxicity or weight loss over the course of the experiment. Additionally, there was no significant difference between the two groups of mice with respect to the mean weights of the heart, liver, and kidney after sacrifice. Taken together, these results suggest that the rhodium(III) complex of Formula II was effective at inhibiting the growth of skin cancer tissue in an in vivo model, without causing overt toxicity to the mice.

Effect on STAT3 Signaling

Because of the critical role of STAT3 in the development skin cancers, the mechanism of action of the compound of Formula II STAT3 signaling was further explored The compound of Formula II inhibited the DNA-binding activity of STAT3 (IC$_{50}$=0.83±0.17 µM) in a cell-free assay. Moreover, this compound suppressed STAT3-directed luciferase reporter activity in EGF-stimulated A375 cells (IC$_{50}$=2.4±0.2 µM), thus indicating that it could suppress STAT3-driven gene transcription in cells. Furthermore, a fluorescence polarization assay revealed that the compound of Formula II was able to displace the high-affinity peptide 5'-FAM-GpYLPQTV from the SH2 domain of STAT3 in a dose-dependent manner, with an IC$_{50}$ value of 4.8 µM, thus suggesting that it targets the SH2 domain of STAT3.

Effect on STAT3 Dimerization

A STAT3 pull-down assay using A375 cells co-expressing FLAG-STAT3 and STAT3-GFP was performed to investigate whether the compound of Formula II could inhibit STAT3 dimerization in cells. In the absence of the compound of Formula II, STAT3-GET co-immunoprecipitated with FLAG-STAT3. A dose-dependent decrease in the level of STAT3-GFP was observed upon treatment of A375 cells with the compound, thus suggesting that the compound was able to disrupt the interaction between STAT3-GFP and FLAG-STAT3 in cells.

It has been reported that phosphorylation of STAT3 monomers is essential for dimerization. Treatment of A375 cells with the compound of Formula II resulted in a dose-dependent reduction in STAT3 tyrosine-705 phosphorylation, but had no effect on total STAT3 content, as observed by Western blotting. The inventors envision that the inhibition of STAT3 tyrosine phosphorylation could be attributed to the targeting of the SH2 domain of STAT3 by the compound of Formula II, which prevents its interactions with pTyr residues on cytoplasmic receptor kinases that are essential for the subsequent phosphorylation. The ability of this compound to inhibit STAT3-driven transcription, STAT3 dimerization, and STAT3 phosphorylation in cells was further confirmed in other cell types. Additionally, unlike previous iridium(III) and rhodium(III) complexes developed by our group, the compound of Formula II showed no significant effect against JAK2 activity, mTOR activity, or TNF-α binding, thus indicating, the importance of chemical structure in determining the selectivity of these substitutionally inert complexes against protein targets. Finally, compound of Formula II possessed a logP value of −0.596, thus indicating that it is relatively hydrophilic and satisfies Lipinski's lipophilicity criterion (logP<5) for drug likeness.

Effect on STAT3 Signaling In Vivo

To investigate whether the compound of Formula II, inhibited STAT3 signaling in vivo, the inventors performed immunohistochemistry experiments on the xenografted tumor tissues after sacrifice. The treated tumor tissues showed significantly reduced levels of phosphorylated STAT3 compared to the vehicle control group, thus suggesting that the anti-tumor activity of the compound of Formula II against human tumor xenografts could be, at least in part, attributed to the suppression of STAT3 activity in vivo. Moreover, the levels of JAK2 phosphorylation were unaffected, which was consistent with the in vitro data described above. Further experiments showed that inflammatory cytokine COX-2 and inducible nitric oxide synthase (iNOS) expression in tumor tissues were reduced.

This observation is consistent with previous reports showing that STAT3 promotes the expression of COX-2 and iNOS. Given the putative roles of COX-2 and iNOS in tumor biology, this result offers another possible avenue by which the compound of Formula II might exert anti-proliferative activities in the mouse model. In contrast, the levels of pro-caspase-3 were not significantly affected by treatment with the compound of Formula II.

Effect on Angiogenesis

Angiogenesis is essential for the growth and metastasis of cancers, and blood flow is increased around tumors compared to surrounding normal tissues. Laser Doppler flowmetry results demonstrated that the blood flow around the tumors of mice in the treatment group was reduced compared that of the vehicle control group. This data suggested that the compound or Formula II was able to, directly or indirectly, inhibit angiogenesis in the mouse xenograft model, thereby potentially depriving tumor tissues of oxygen and nutrients necessary for proliferation.

Microarray analysis revealed that the focal adhesion, cytokine-cytokine receptor interaction, and leukocyte transendothelial migration pathways contained multiple downregulated genes in tumor tissues of the treatment group compared to the control group (see Table S3). The downregulation of VEGF C is particularly noteworthy as VEGF is a well-known promoter of angiogenesis. Significantly, STAT3 has been reported to up-regulate VEGF expression and tumor angiogenesis in human cancer cell lines and in non-small-cell lung carcinoma patients. The inventors believe that the down-regulation of VEGF expression in tumor tissues could be attributed to the inhibition of STAT3-directed transcription by the compound of Formula II in vivo, which could, in turn, account for the reduction of blood flow in the treated mice as observed by laser Doppler flowmetry.

While the invention has been described by means of specific embodiments and applications thereof, it is understood that numerous modifications and variations could be made thereto by those skilled in the art without departing from the spirit and scope of the invention as defined by the following claims.

The invention claimed is:

1. A compound of the formula:

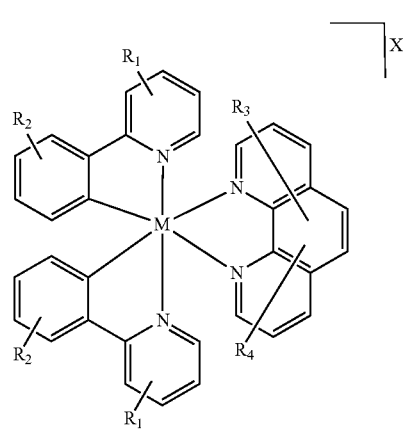

Formula I wherein

M represents rhodium;

X represents an anion selected from the group consisting of fluorine, chlorine, bromine, nitrate, tetrafluoroborate, hexafluorophosphate ($PF_6$), trifluoromethane sulfonate, trifluoromethane sulfonimide, acetate, trifluoroacetate, tetraphenyl borate, toluene sulfonate, dodecylbenzene sulfonate or mixtures thereof;

$R^1$ represents H or F;

$R^2$ represents H, F, or —CH=O;

or $R^1$ and $R^2$ together represent —CH=CH—; and $R^3$ and $R^4$ are methyl.

2. A compound as claimed in claim 1 wherein X is $PF_6$.

3. A compound as claimed in claim 1 wherein $R^1$ is hydrogen.

4. A compound of the formula:

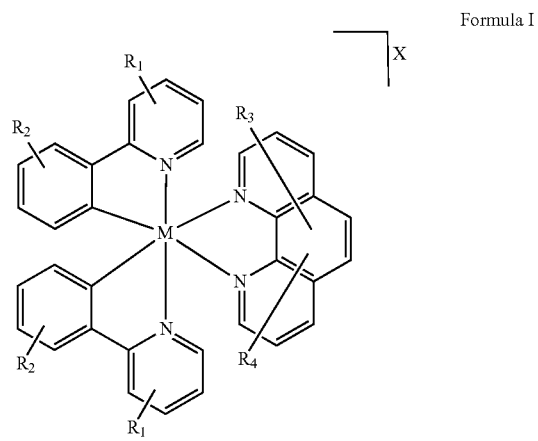

Formula I wherein

M represents iridium or rhodium;

X represents an anion selected from the group consisting of fluorine, chlorine, bromine, nitrate, tetrafluoroborate, hexafluorophosphate ($PF_6$), trifluoromethane sulfonate, trifluoromethane sulfonimide, acetate, trifluoroacetate, tetraphenyl borate, toluene sulfonate, dodecylbenzene sulfonate or mixtures thereof;

$R^1$ represents H or F;

$R^3$ and $R^4$ are methyl; and wherein $R^2$ is CHO.

5. A compound as claimed in claim 1, wherein $R^3$ and $R^4$ are bound to the central ring of the phenanthroline ligand.

6. A compound as claimed in claim 1, wherein

M represents rhodium;

X represents an anion which is hexafluorophosphate ($PF_6$);

$R^1$ represents H;

$R^2$ represents —CH=O; and $R^3$ and $R^4$ are methyl.

7. A method for antagonizing STAT3 dimerization in a patient in need thereof which comprises administering to such patient a therapeutically acceptable dose of a compound of the formula:

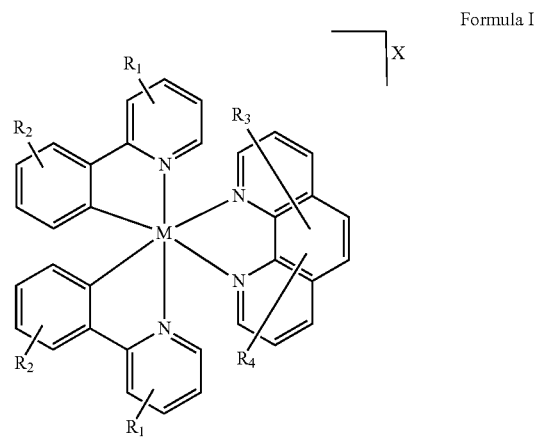

Formula I wherein

M represents iridium or rhodium;

X represents an anion selected from the group consisting of fluorine, chlorine, bromine, nitrate, tetrafluoroborate, hexafluorophosphate ($PF_6$), trifluoromethane sulfonate, trifluoromethane sulfonimide, acetate, trifluoroacetate, tetraphenyl borate, toluene sulfonate, dodecylbenzene sulfonate or mixtures thereof;

$R^1$ represents H or F;

$R^2$ represents H, F, or —CH═O;

or $R^1$ and $R^2$ together represent —CH═CH—; and $R^3$ and $R^4$ are methyl.

8. A method as claimed in claim 7 wherein the compound used is one wherein M is rhodium.

9. A method as claimed in claim 7 wherein the compound used is one wherein X is $PF_6$.

10. A method as claimed in claim 7 wherein the compound used is one wherein $R^1$ is hydrogen.

11. A method as claimed in claim 7 wherein the compound used is one wherein $R^2$ is CHO.

12. A method as claimed in claim 7, wherein $R^3$ and $R^4$ are bound to the central ring of the phenanthroline ligand.

13. A method for treating a cancer patient in need thereof by administering a therapeutically effective dose of a compound of the formula

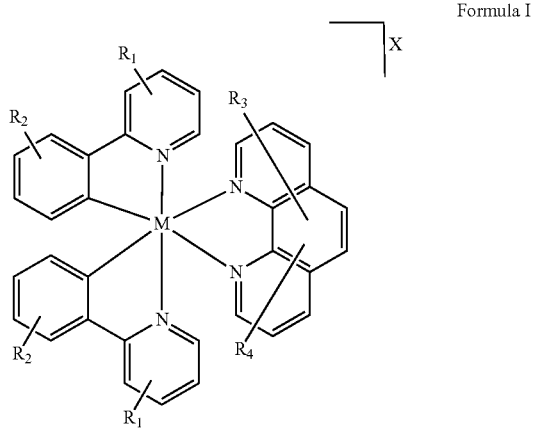

Formula I wherein

M represents iridium or rhodium;

X represents an anion selected from the group consisting of fluorine, chlorine, bromine, nitrate, tetrafluoroborate, hexafluorophosphate ($PF_6$), trifluoromethane sulfonate, trifluoromethane sulfonimide, acetate, trifluoroacetate, tetraphenyl borate, toluene sulfonate, dodecylbenzene sulfonate or mixtures thereof;

$R^1$ represents H or F;

$R^2$ represents H, F, or —CH═O;

or $R^1$ and $R^2$ together represent —CH═CH—; and $R^3$ and $R^4$ are methyl.

14. A method as claimed in claim 13 wherein said cancer is selected from the group consisting of nonsmall cell lung carcinoma, breast cancer, colorectal cancer, ovarian cancer, cervical cancer, hepatocellular cancer and skin cancer.

15. A method as claimed in claim 13 wherein the compound used is one wherein M is rhodium.

16. A method as claimed in claim 13 wherein the compound used is one wherein X is $PF_6$.

17. A method as claimed in claim 13 wherein the compound used is one wherein $R^1$ is hydrogen.

18. A method as claimed in claim 13 wherein the compound used is one wherein $R^2$ is CHO.

19. A method as claimed in claim 13 wherein the compound used is one wherein $R^3$ and $R^4$ are bound to the central ring of the phenanthroline ligand.

20. A method for antagonizing STAT3 dimerization in a patient in need thereof which comprises administering to such patient a therapeutically acceptable dose of the compound of claim 6.

21. A method for treating a cancer patient in need thereof by administering a therapeutically effective dose of the compound of claim 6.

22. The method according to claim 21, wherein said cancer is selected from the group consisting of nonsmall cell lung carcinoma, breast cancer, colorectal cancer, ovarian cancer, cervical cancer, hepatocellular cancer and skin cancer.

* * * * *